United States Patent [19]

Beach et al.

[11] 4,301,318

[45] Nov. 17, 1981

[54] PROCESS FOR RECOVERING OLIGOMERIZATION PRODUCT

[75] Inventors: David L. Beach, Gibsonia; James J. Harrison, Glenshaw, both of Pa.

[73] Assignee: Gulf Research & Development Company, Pittsburgh, Pa.

[21] Appl. No.: 210,413

[22] Filed: Nov. 25, 1980

Related U.S. Application Data

[63] Continuation-in-part of Ser. No. 179,080, Aug. 18, 1980, Ser. No. 179,079, Aug. 18, 1980, Ser. No. 179,078, Aug. 18, 1980, Ser. No. 179,076, Aug. 18, 1980, and Ser. No. 179,005, Aug. 18, 1980.

[51] Int. Cl.³ .......................... C07C 2/02; C07C 2/26
[52] U.S. Cl. .................................... 585/526; 585/511; 585/528; 585/531
[58] Field of Search ............... 585/526, 528, 531, 511

[56] References Cited

U.S. PATENT DOCUMENTS 2,998,416  8/1961  Mendel ............................... 526/100
3,686,159  8/1972  Bauer et al. ......................... 526/96

OTHER PUBLICATIONS

Keim et al., "Novel Coordination of (Benzoylmethylene)triphenylphosphorane in a Nickel Oligomerization Catalyst", *Agnew. Chem. Int. Ed. Engl.*, vol. 17, No. 6, pp. 466 and 467 (1978).

*Primary Examiner*—Curtis R. Davis
*Attorney, Agent, or Firm*—Deane E. Keith; Forrest D. Stine; Joseph J. Carducci

[57] ABSTRACT

Ammonium hydroxide is used to remove nickel ylide residue from an oligomerization reaction product obtained by contacting ethylene with a nickel ylide catalyst under oligomerization conditions. The oligomerization reaction product is contacted with ammonium hydroxide to obtain a product composed of two layers, an upper layer containing normal alpha olefins and a lower layer containing nickel ylide residue. The two layers are then separated from each other to recover the desired normal alpha olefins.

62 Claims, No Drawings

PROCESS FOR RECOVERING OLIGOMERIZATION PRODUCT

CROSS-REFERENCES TO RELATED APPLICATIONS

This application is a continuation-in-part of our U.S. patent application Ser. No. 179,079, filed Aug. 18, 1980, entitled "Nickel Ylides"; U.S. patent application Ser. No. 179,075, filed Aug. 18, 1980, entitled "Process for the Preparation of Nickel Ylides Containing Sulfonated Group V Ligands"; U.S. patent application Ser. No. 179,080, filed Aug. 18, 1980, entitled "Process for the Preparation of Nickel Ylides Containing Ylide Ligands With a Sulfonated Group V Component"; U.S. patent application Ser. No. 179,078, filed Aug. 18, 1980, entitled "Process for the Preparation of Nickel Ylides Containing Directly Sulfonated Ylide Ligands"; U.S. patent application Ser. No. 179,076, filed Aug. 18, 1980, entitled "Process for the Oligomerization of Ethylene"; and U.S. patent application Ser. No. 179,005, filed Aug. 18, 1980, entitled "Process for the Oligomerization of Ethylene in Methanol".

Reference is made to applicants' following U.S. applications:

U.S. patent application Ser. No. 209,673, filed Nov. 24, 1980, entitled "Novel Group VA Salts and Process for Preparing Same".

U.S. patent application Ser. No. 210,283, filed Nov. 25, 1980, entitled "Novel Group VA Ylides and Process for Preparing Same."

U.S. patent application Ser. No. 209,674, filed Nov. 24, 1980, entitled "Sulfonated Group VA Ylides and Process for Preparing Same".

The disclosures of the foregoing applications are hereby incorporated by reference.

FIELD OF THE INVENTION

The present invention relates to the use of ammonium hydroxide to remove nickel ylide residue from an oligomerization reaction product obtained by contacting ethylene with a nickel ylide catalyst under oligomerization conditions.

DESCRIPTION OF THE PRIOR ART

It is well known in the art to use a variety of catalysts to oligomerize ethylene to higher molecular weight olefins. The term "oligomerize" has been employed, and is employed herein to describe the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyls or alkyl halides and titanium halides. Major disadvantages of aluminum alkyl catalysts are their highly reactive and pyrophoric nature and the fact that they must be used at relatively high temperatures, e.g., 200°–275° C. and pressures, e.g., 2000–4000 psig (13,790 to 27,580 kPa). Although much milder reaction conditions are used when the aluminum alkyls are used in conjunction with titanium halides, product quality and ease of catalyst separation from products of both of these prior art types of catalysts are not as high as desired.

An article by W. Keim, F. H. Kowaldt, R. Goddard and C. Kruger entitled "Novel Coordination of (Benzoylmethylene)triphenylphosphorane in a Nickel Oligomerization Catalyst", in Angew. Chem. Int. Ed. Engl. (1978) No. 6, page 466, discloses that a nickel ylide having the structure:

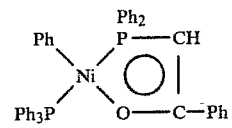

converts ethylene into alpha olefins or polyethylene.

SUMMARY OF THE INVENTION

It has now been found that ammonium hydroxide can be used to remove nickel ylide residue from an oligomerization reaction product obtained by contacting ethylene with a nickel ylide catalyst under oligomerization conditions. The nickel ylide catalyst used in the oligomerization reaction is defined by the following Formula I:

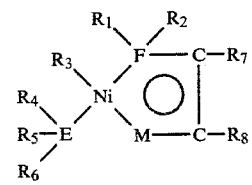

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbons atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hyroxyl group; an alkoxy or aryloxy group; and a hydrocarbyl group, such as defined above, carrying halogen, hydroxyl, alkoxy or aryloxy; provided that at least one, preferably from about one to about four, of each of $R_1$ to $R_8$ is a sulfonato group ($-SO_3^-$) or an alkyl, aryl, alkenyl, cycloalkyl, aralkyl or alkaryl group carrying a sulfonato group; M is sulfur or oxygen, preferably oxygen; E is phosphorus, arsenic, antimony or nitrogen, preferably phosphorus; and F is phosphorus, arsenic or antimony, preferably phosphorus. The oligomerization reaction product is contacted with ammonium hydroxide to obtain a product composed of two layers, an upper layer containing normal alpha olefins and a lower layer containing nickel ylide residue. The two layers are then separated from each other to recover the desired normal alpha olefins.

Specific examples of nickel ylides which may be used in the oligomerization reaction are set forth in Table I. In this table and as used elsewhere herein, "Ph" represents phenyl and "Et" represents ethyl.

TABLE I

| Compound | R₁ | R₂ | R₃ | R₄ | R₅ | R₆ | R₇ | R₈ | E | F | M |
|---|---|---|---|---|---|---|---|---|---|---|---|
| 1 | Ph | Ph | Ph | Ph | Ph | Ph | SO₃⁻ | Ph | P | P | O |
| 2 | Ph | Ph | Ph | Ph | Ph | Ph | H | Ph | P | P | O |
| 3 | 3-(SO₃⁻)-4-MeC₆H₃ | Ph | Ph | Ph | Ph | Ph | H | Ph | P | P | O |
| 4 | Ph | Ph | Ph | 3-(SO₃⁻)-4-MeC₆H₃ | Ph | Ph | H | Ph | P | P | O |
| 5 | Ph | Ph | Ph | Ph | 3-(SO₃⁻)-4-MeC₆H₃ | Ph | H | Ph | P | P | O |
| 6 | Ph | Ph | Ph | Ph | Ph | 3-(SO₃⁻)-4-MeC₆H₃ | SO₃⁻ | Ph | P | P | O |
| 7 | Ph | Ph | Ph | Ph | Ph | Ph | SO₃⁻ | Ph | P | P | O |
| 8 | Ph | Ph | Ph | Ph | Ph | Ph | SO₃⁻ | Ph | As | P | S |
| 9 | Ph | Ph | Ph | CH₂Ph | CH₂Ph | CH₂Ph | SO₃⁻ | Ph | P | P | O |
| 10 | Ph | Ph | Ph | Ph | Ph | Ph | SO₃⁻ | H | P | P | O |
| 11 | Ph | Ph | Ph | Ph | Ph | Ph | SO₃⁻ | CH₃ | P | P | O |
| 12 | Ph | Ph | Ph | Ph | Ph | Ph | SO₃⁻ | Ph—Ph | P | P | O |
| 13 | Et | Et | Ph | Ph | Ph | Ph | H | Ph | P | P | O |
| 14 | Ph | Ph | Ph | Et | Et | Et | SO₃⁻ | Ph | N | P | O |
| 15 | Ph | Ph | Ph | Ph | Ph | Ph | SO₃⁻ | Ph | Sb | P | O |
| 16 | Ph | Ph | Ph | 4-ClC₆H₄ | 4-ClC₆H₄ | 4-ClC₆H₄ | SO₃⁻ | Ph | P | P | O |
| 17 | Ph | Ph | Ph | Ph | Ph | Ph | (CH₂)₃CH₂—SO₃⁻ | Ph | P | P | O |
| 18 | H | H | H | Ph | Ph | Ph | SO₃⁻ | Ph | P | P | O |
| 19 | Ph | Ph | Ph | Ph | 3-(SO₃⁻)-4-MeC₆H₃ | 3-(SO₃⁻)-4-MeC₆H₃ | SO₃⁻ | Ph | P | As | O |
| 20 | Ph | Ph | Ph | Ph | Ph | Ph | Ph | CH₃ | P | P | S |
| 21 | Ph | Ph | Ph | Ph | Ph | Ph | H | OCH₃ | P | P | O |
| 22 | Ph | Ph | Ph | Ph | Ph | Ph | H | OCH₃ | P | P | O |
| 23 | Ph | Ph | 3-(SO₃⁻)-4-MeC₆H₃ | Ph | Ph | Ph | SO₃⁻ | OEt | As | P | O |
| 24 | Ph | CH₃ | Ph | Ph | Ph | Ph | H | OC₄H₉ | P | P | S |

TABLE I-continued

| Compound | R₁ | R₂ | R₃ | R₄ | R₅ | R₆ | R₇ | R₈ | E | F | M |
|---|---|---|---|---|---|---|---|---|---|---|---|
| 25 | CH₃ | CH₃ | CH₃ | Ph |  | Ph | SO₃⁻ | OCH₃ | P | As | O |
| 26 | Ph | Ph | Ph | Ph | Ph | Ph | H |  | P | P | O |
| 27 | Ph |  | Ph | Ph | Ph | Ph | SO₃⁻ |  | P | P | O |
| 28 | Ph |  | Ph | Ph | Ph | Ph | H | OC₃H₇ | As | P | S |
| 29 | Ph | CH₃ | Ph |  | Ph | Ph | H | CH₃ | P | As | O |
| 30 | Ph | Ph | Ph | cyclohexyl | cyclohexyl | cyclohexyl | SO₃⁻ | CH₃ | As | P | O |
| 31 | CH₃ | CH₃ | CH₃ | Et | Et | Et | SO₃⁻ | OC₄H₉ | P | P | O |
| 32 | CH₃ | CH₃ | CH₃ | Et | Et | Et | H | OC₄H₉ | P | P | O |
| 33 | Ph | CH₃ | CH₃ | CH₃ | CH₃ | CH₃ | SO₃⁻ | CH₃ | As | As | S |
| 34 | Ph |  | Ph | Ph | Ph | Ph | H |  | P | P | O |
| 35 | CH₃ | Et | Ph |  |  | Ph | SO₃⁻ |  | As | As | S |
| 36 | H | Ph | Ph | Ph | Ph | Ph | SO₃⁻ | CH₃ | P | P | O |
| 37 | Ph | Et | Et | Ph | Ph | Ph | SO₃⁻ | CH₃ | As | As | S |
| 38 | H | H | H | H | H | H | H | H | P | P | O |
| 39 | Ph | Ph | Ph | Ph | Ph | Ph | SO₃⁻ | OCH₃ | P | As | O |
| 40 | Ph | Ph | Ph | butyl | butyl | butyl | SO₃⁻ | Ph | P | As | O |

DESCRIPTION OF THE PREFERRED EMBODIMENTS

In obtaining the oligomerization reaction product, the nickel ylide is preferably dissolved in an appropriate solvent or carrier, such as toluene, dioxane, tetrahydrofuran, anisole, methanol, etc. A portion of the oligomer product can suitably serve as at least a part of the reactor diluent. The order of addition of the components (ethylene, catalyst and solvent) to the reaction zone is not critical, although it is preferred that catalyst and solvent first be heated to reaction temperature and then to add rapidly ethylene to the desired pressure. The reaction can be carried out in any manner that assures contact between ethylene and catalyst, for example, in a batch reactor or in a continuous stirred tank reactor.

The amount of nickel ylide catalyst used will be such that its concentration in the solvent will be in the range of about 0.0001 to about 1.0 mole per liter of solvent, preferably in the range of about 0.0005 to about 0.1 mole per liter of solvent. Ethylene is added to the reaction zone as needed, but throughout the reaction the ethylene pressure is maintained in the range of about 10 to about 700 pounds per square inch gauge (68.9 to 4826 kPa), preferably about 300 to about 600 pounds per square inch gauge (2069 to 4137 kPa), most preferably about 350 to about 550 pounds per square inch gauge (2413 to 3792 kPa). The reaction temperature can be in the range of about $-20°$ to about 200° C., preferably in the range of about 20° to about 100° C. The contact time (the length of time between the exposure of catalyst to ethylene and the separation of unreacted ethylene and/or reaction product from the catalyst) can be in the range of about one minute to about 72 hours, preferably in the range of about 10 minutes to about 24 hours. Throughout the reaction period the reaction mixture is agitated. Ethylene conversion under optimum reaction conditions can be in excess of about 90 percent and can reach up to about 99 percent.

At the end of the reaction period, the gaseous components that may be present in the reaction product, for example, unreacted ethylene, $C_4$ olefins, etc., are flashed therefrom and ethylene recycled to the reaction zone if desired.

The total reaction product remaining containing solvent or carrier, oligomerization reaction product and catalyst is then treated with an ammonium hydroxide solution. If desired, prior to such treatment, the solvent used in the oligomerization reaction can be removed from the reaction product. This can be done, for example, by subjecting the oligomerization reaction product to distillation. Depending upon the boiling point of the solvent, some of the lower normal alpha olefin products in the oligomerization reaction product may be removed from the oligomerization reaction product prior to removal of solvent therefrom. This will not adversely affect the treatment of the remainder of the oligomerization reaction product with the ammonium hydroxide solution.

The amount of ammonium hydroxide solution used to treat the oligomerization reaction product can vary widely, but, in general, should be at least about 0.1 milliliters of ammonium hydroxide, as 100 percent ammonium hydroxide, per 100 milliliters of oligomerization reaction product being treated, but preferably should be in the range of about five to about 50 milliliters of ammonium hydroxide per 100 milliliters of oligomerization reaction product. In a preferred embodiment an aqueous ammonium hydroxide solution containing from about one to about 50 volume percent water, preferably containing from about 10 to about 35 percent water, is used.

The treatment is simply effected. For example, the ammonium hydroxide solution and the oligomerization reaction product are brought into contact with each other and then vigorously agitated, for example, for at least about 10 seconds, preferably for about one to about five minutes. The components of the mixture can be maintained in the temperature range of about 0° to about 30° C., preferably about 25° C., and in the pressure range of about 15 to about 2500 pounds per square inch gauge (103.4 to 17238 kPa), preferably about atmospheric pressure.

As a result of the above described treatment, a product is obtained consisting of two distinct liquid phases, (1) an upper phase containing the desired oligomer product, solvent if not previously removed and dissolved non-nickel residues of the nickel ylide catalysts, and (2) a lower phase containing ammonium hydroxide, water if aqueous ammonium hydroxide has been used, nickel residues of the nickel ylide catalyst and other non-nickel residues of the nickel ylide catalyst.

Referring to the upper liquid phase defined above and to the nickel ylide catalyst previously defined with respect to Formula I, the nickel ylide residues in the upper phase are compounds containing E (phosphorous, arsenic, antimony or nitrogen) of F (phosphorus, arsenic or antimony). Some of these same residues are also found in the lower phase. The upper phase will contain from about 30 to about 75 weight percent of the total of these residues. In addition, the lower phase will also contain substantially all (more than 90 weight percent) of whatever nickel-containing residues are present in the oligomerization reaction product.

The two phases defined above can be separated from each other by any conventional manner, for example, by decantation or by use of a separatory funnel. The components in the upper phase, that is, individual oligomer products, fractions of oligomer products, solvents if present, and the defined metal residues, can be separated from each other and/or recovered by any conventional means, for example, by distillation. The lower phase can be discarded.

The nickel ylide catalyst used in the process of this invention can be prepared using several different procedures. The following procedure, Procedure I, relates to the preparation of nickel ylides wherein the sulfonato group is located in $R_4$, $R_5$ and/or $R_6$ and at least one of $R_4$, $R_5$ and $R_6$ is aryl.

The first step in Procedure I involves sulfonating a ligand defined by the formula:

wherein $R_4$ to $R_6$ and E are as defined above, provided that at least one of $R_4$, $R_5$ and $R_6$ is an aryl group as defined above using $SO_3$ in the presence of a strong inorganic mineral acid, such as sulfuric acid, hydrochloric acid, nitric acid, phosphoric acid, etc. Specific examples of such ligands that can be used include: allyldiphenylphosphine; benzyldiphenylphosphine; bis(3-aminopropyl)phenylphosphine; bis(2-cyanoethyl)- phenylphosphine; bis(m-fluorophenyl)phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; dicyclohexylphenylphosphine; di-ethylphenylphosphine; di-n-heptylphenylphosphine; di-n-hexylphenylphosphine; dimethylphenylphosphine; dimethyl-p-tolylphosphine; diphenyl-n-butoxyphosphine; diphenylchlorophosphine; diphenylenephenylphosphine; diphenylethoxyphosphine; diphenylmethoxyphosphine; diphenylphosphine; beta-diphenylphosphinoethyltriethoxysilane; di-iso-propylphenylphosphine; di-o-tolylphenylphosphine; divinylphenylphosphine; ethyldiphenylphosphine; n-hexyldiphenylphosphine; omethoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyl-di-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tri(1naphthyl)phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolyphosphine; tri-p-tolylphosphine; vinyldiphenylphosphine; sodium diphenylphosphinebenzene-3-sulfonate; disodium phenylphosphinebis(benzene-3-sulfonate); dimethylphenylarsine; methyldiphenylarsine; triphenylarsine; tri-p-tolylarsine; diphenylchloroarsine; triphenylantimony; triphenylamine; tribenzylamine; methyldiphenylamine; and dimethylphenylamine.

It is preferred to use fuming sulfuric acid ($H_2SO_4 \cdot xSO_3$, where x can be, for example, from about 0.1 to about 0.6, preferably from about 0.2 to about 0.4). The amount of $SO_3$ is not critical and can vary over a wide range, for example, at least about one mole per mole of ligand, preferably from about two to about 20 moles per mole of ligand. The two reactants are stirred and heated at a temperature of about 0° to about 200° C., preferably about 40° to about 100° C., for about one minute to about 48 hours, preferably for about 30 minutes to about four hours. Any suitable pressure can be used, although atmospheric pressure is preferred. At the end of this period the reactor contents are cooled to a temperature of about −30° to about 50° C., preferably about room temperature (about 26° C.), after which sufficient water and a suitable base, such as an alkaline metal hydroxide, an alkali metal alkoxide, ammonium hydroxide, a hydrocarbyl-substituted ammonium hydroxide, etc. are added thereto to crystallize the sulfonated ligand out of solution. For example, the amount of water used can range from about 10 milliliters to about 10 liters per mole of sulfonated ligand. The crystals can be recovered in any suitable manner, for example, by filtration, decantation or by centrifuging.

In the second step of Procedure I, the sulfonated ligand obtained in the first step is reacted with any zero valent nickel compound, or any nickel compound convertible to a zero valent nickel compound in situ, and a ylide defined by the following Formula II:

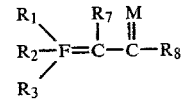

wherein $R_1$, $R_2$, $R_3$, $R_7$, $R_8$, M and F are as defined above. Specific examples of such nickel compounds which can be used include: tris(triphenylphosphine)nickel; bis(cyclooctadiene)nickel; tetrakis(triphenylphosphine)nickel; bis(norbornadiene)nickel; (cycloocta-1,5-diene)duroquinone nickel; (dicyclopentadiene)duroquinone nickel; bis(tetracyclone)nickel; tetrakis(triethylphosphine)nickel; tris(triethylphosphine)nickel; bis(triphenylphosphine)nickel dicarbonyl; nickel carbonyl; nickel(II)acetylacetonate; nickelocene; bis(triethylphosphine)nickel(II)chloride; tetrakis(trifluorophosphine)nickel; nickel acetate; nickel bromide; nickel carbonate; nickel chloride; nickel fluoride; nickel iodide, nickel nitrate; nickel sulfate; nickel 2,4-pentanedionate, bis π-allyl nickel; and nickel dichloride hexaamine. Specific examples of ylides coming within the definition of Formula II are set forth in Table II.

TABLE II

| Compound | $R_1$ | $R_2$ | $R_3$ | $R_7$ | $R_8$ | F | M |
|---|---|---|---|---|---|---|---|
| 1 | Ph | Ph | Ph | H | Ph | P | O |
| 2 | Ph | Ph | Ph | H | Ph | P | S |
| 3 | Ph | Ph | Ph | $SO_3^-$ | Ph | P | O |
| 4 | Ph | Ph | Ph | $SO_3^-$ | Ph | P | S |
| 5 | –C$_6$H$_4$–SO$_3^-$ | Ph | Ph | H | Ph | P | O |
| 6 | Ph | –C$_6$H$_4$–SO$_3^-$ | Ph | $SO_3^-$ | Ph | P | S |
| 7 | Ph | Ph | Ph | H | OCH$_3$ | P | O |
| 8 | Ph | Ph | Ph | $SO_3^-$ | OCH$_3$ | R | O |
| 9 | Ph | Ph | Ph | H | OCH$_3$ | P | S |
| 10 | –C$_6$H$_4$–SO$_3^-$ | Ph | Ph | H | OCH$_3$ | P | O |
| 11 | Ph | –C$_6$H$_4$–SO$_3^-$ | Ph | $SO_3^-$ | OCH$_3$ | P | O |
| 12 | Ph | Ph | Ph | H | CH$_3$ | P | O |
| 13 | Ph | Ph | Ph | $SO_3^-$ | OCH$_3$ | P | O |

TABLE II-continued

| Compound | R₁ | R₂ | R₃ | R₇ | R₈ | F | M |
|---|---|---|---|---|---|---|---|
| 14 | -C₆H₄-SO₃⁻ | Ph | Ph | H | CH₃ | P | O |
| 15 | Ph | -C₆H₄-SO₃⁻ | Ph | SO₃⁻ | CH₃ | P | O |
| 16 | Ph | Ph | Ph | SO₃⁻ | CH₃ | P | S |
| 17 | Ph | Ph | Ph | H | CH₃ | P | O |
| 18 | CH₃ | CH₃ | CH₃ | H | Ph | P | O |
| 19 | CH₃ | CH₃ | CH₃ | SO₃⁻ | Ph | P | O |
| 20 | CH₃ | CH₃ | CH₃ | H | Ph | P | S |
| 21 | CH₃ | CH₃ | CH₃ | SO₃⁻ | Ph | P | S |
| 22 | Et | Et | Et | SO₃⁻ | Ph | P | O |
| 23 | CH₃ | -C₆H₄-SO₃⁻ | Et | H | Ph | P | O |
| 24 | CH₃ | Cyclohexyl | Ph | SO₃⁻ | Ph | P | S |
| 25 | CH₃ | CH₃ | CH₃ | H | OCH₃ | P | O |
| 26 | CH₃ | Ph | Et | SO₃⁻ | CH₃ | P | O |
| 27 | -C₆H₄-SO₃⁻ | Ph | Et | H | OCH₃ | P | S |
| 28 | CH₃ | CH₃ | CH₃ | H | CH₃ | P | O |
| 29 | Ph | CH₃ | Et | SO₃⁻ | CH₃ | P | O |
| 30 | Ph | -C₆H₄-SO₃⁻ | CH₃ | H | CH₃ | P | S |
| 31 | Ph | Ph | Et | SO₃⁻ | CH₃ | P | S |
| 32 | -C₆H₄-SO₃⁻ | CH₃ | Et | SO₃⁻ | CH₃ | P | O |
| 33 | -C₆H₄-Cl | Ph | Ph | SO₃⁻ | Ph | P | O |
| 34 | -C₆H₄-Cl | Ph | CH₃ | H | Ph | P | S |
| 35 | CH₃ | CH₃ | Et | SO₃⁻ | -C₆H₄-Cl | P | O |
| 36 | Ph | Ph | Ph | H | Ph | As | O |
| 37 | Ph | Ph | Ph | H | Ph | As | S |
| 38 | Ph | Ph | Ph | SO₃⁻ | Ph | As | O |
| 39 | Ph | Ph | Ph | SO₃⁻ | CH₃ | As | O |
| 40 | CH₃ | CH₃ | CH₃ | H | Ph | As | O |
| 41 | Ph | CH₃ | CH₃ | SO₃⁻ | Ph | As | O |
| 42 | Ph | -C₆H₄-SO₃⁻ | CH₃ | H | Ph | As | O |
| 43 | Ph | Ph | Ph | H | Ph | Sb | O |
| 44 | Ph | Ph | Ph | SO₃⁻ | Ph | Sb | O |
| 45 | Ph | -C₆H₄-SO₃⁻ | Ph | H | Ph | Sb | O |
| 46 | Ph | -C₆H₄-SO₃⁻ | Ph | SO₃⁻ | Ph | Sb | O |
| 47 | Ph | Ph | Ph | H | Ph | Sb | O |
| 48 | Ph | Ph | Ph | SO₃⁻ | Ph | Sb | S |
| 49 | CH₃ | CH₃ | CH₃ | H | Ph | Sb | O |
| 50 | CH₃ | Ph | CH₃ | SO₃⁻ | Ph | Sb | O |
| 51 | Ph | Ph | Ph | H | O-C₆H₄-SO₃⁻ | P | O |
| 52 | Ph | Ph | Ph | H | O-C₆H₄-SO₃⁻ | P | S |
| 53 | Ph | -C₆H₄-SO₃⁻ | Ph | H | OC₃H₇ | P | O |
| 54 | Ph | Ph | Ph | SO₃⁻ | OC₄H₉ | P | O |
| 55 | Ph | Ph | Ph | SO₃⁻ | O-C₆H₄-SO₃⁻ | P | O |

TABLE II-continued

| Compound | R₁ | R₂ | R₃ | R₇ | R₈ | F | M |
|---|---|---|---|---|---|---|---|
| 56 | Ph | Ph | Ph | H | 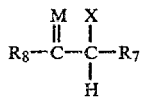 | As | O |

In this second step approximately equal molar amounts of each of the three reactants defined above are dissolved in any suitable unreactive solvent, such as toluene, tetrahydrofuran, dioxane, or other unreactive hydrocarbon solvents, and stirred while maintaining a temperature of about 0° to about 100° C., preferably room temperature, for about one-half hour to about 48 hours, preferably about three to about 20 hours, sufficient to ensure complete reaction. Any suitable pressure can be used, although atmospheric pressure is preferred. The solvent can be removed from the reaction mixture in any suitable manner, for example, by distillation, including vacuum distillation, if necessary, leaving behind the compound defined above. On the other hand, a second solvent in which the desired product is insoluble, such as heptane, can be added to the reaction product to precipitate the compound therein. The compound can be recovered, for example, by filtration, decantation or by centrifuging.

The following procedure, Procedure II, relates to the preparation of nickel ylides wherein the sulfonato group is located in $R_1$, $R_2$, and/or $R_3$. In this procedure, the first step involves reacting a ligand, defined by the formula:

wherein $R_1$, $R_2$, $R_3$ and F are as defined above, provided that at least one of $R_1$, $R_2$ and $R_3$ is a sulfonato group or an alkyl, aryl, alkenyl, cycloalkyl, aralkyl or alkaryl, as defined above, carrying a sulfonato group, with an alpha substituted ketone or aldehyde or an alpha substituted thioketone or thioaldehyde defined by the following formula:

$$R_8-\overset{M}{\overset{\|}{C}}-\underset{H}{\overset{X}{\underset{|}{C}}}-R_7$$

wherein $R_7$, $R_8$ and M are as defined above and X is a halogen radical selected from the group consisting of fluorine, chlorine, bromine and iodine, preferably chlorine and bromine, a tosyl group (a toluene sulfonate group), or an acetate group. The sulfonated ligand can be obtained in any conventional manner by sulfonating the appropriate trihydrocarbyl phosphine, arsine or stibine or by sulfonating using the procedure employed in Procedure I. Specific examples of ligands that can be used include: allyldiphenylphosphine; benzyldiphenylphosphine; bis(3-aminopropyl)phenylphosphine; bis(2-cyanoethyl)phenylphosphine; bis(m-fluorophenyl)phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; di-cyclohexylphenylphosphine; di-ethylphenylphosphine; di-n-heptylphenylphosphine; di-n-hexylphenylphosphine; di-methylphenylphosphine; dimethyl-p-tolylphosphine; di-phenyl-n-butoxyphosphine; diphenylchlorophosphine; di-phenylenephenylphosphine; diphenylethoxyphosphine; di-phenylmethoxyphosphine; diphenylphosphine; beta-diphenylphosphinoethyltriethoxysilane; di-iso-propylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyldi-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tris(1-naphthyl)phosphine; triphenylphosphine; tris(4-dimethylaminophenyl)phosphine; tris(p-fluorophenyl)phosphine; tris(O-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphinebis(benzene-3-sulfonate); dimethylphenylarsine; methyldiphenylarsine; triphenylarsine; tri-p-tolylarsine; diphenylchloroarsine; and triphenylantimony. Specific examples of such alpha substituted ketones or aldehydes and of alpha substituted thioketones or thioaldehydes that can be used herein include: phenacylchloride; phenacylbromide; alpha-acetoxyacetophenone; alpha-bromo-2'-acetonaphthone; alpha-bromoacetone; 3-bromocamphor; alpha-bromo-p-chloroacetophenone; alpha-bromo-2',4'-dimethoxyacetophenone; alpha-bromoiosbutyrophenone; alpha-bromo-o-methoxyacetophenone; alpha-bromo-m-methoxyacetophenone; alpha-bromo-p-methoxyacetophenone; alpha-bromo-4'-methylacetophenone; p-bromo-phenacrylbromide; alpha-bromopropiophenone; chloroacetone; alpha-chloro-p-fluoroacetophenone; alpha-chlorobutyrophenone; p-chlorophenacylchloride; alpha-chloropropiophenone; alpha-chlorothioacetophenone; alpha-bromothioacetophenone; alpha-chloroethylnaphthylketone; alphachloromethylacetate; alpha-bromomethylacetate; alphachloroethylacetate; alpha-bromoethylacetate; alpha-chloropropylacetate; alpha-chlorobutylacetate; alpha-chlorophenylacetate; alpha-chloro-p-sulfonatophenylacetate; alpha-bromopropylacetate; alpha-bromobutylacetate; alpha-bromophenylacetate; and alpha-bromo-p-sulfonatophenylacetate.

The reaction between the sulfonated ligand and the ketone or aldehyde is carried out using about equal molar amounts of each reactant while they are dissolved in an appropriate hydrocarbon solvent, such as toluene or tetrahydrofuran, and the reaction is carried out at a temperature of about 20° to about 200° C., preferably about 50° to about 150° C., and any suitable pressure, preferably atmospheric, for about one to about 24 hours, preferably for about two to about eight hours. The reaction mixture is then cooled, preferably to room temperature. If a solid results from such cooling it is recovered in any suitable manner, for example, by filtration, decantation or by centrifuging. If solids do not form, the reaction mixture can be subjected to distillation to remove solvents therefrom, leaving behind solid material, which is a salt defined by the following Formula III:

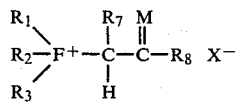

wherein $R_1$, $R_2$, $R_3$, $R_7$, $R_8$, F, M and X are as defined in the previous paragraph.

To convert the above salt to the corresponding ylide, the salt is reacted with a stoichiometric amount of a base, such as an alkali metal hydroxide (sodium or potassium hydroxide), an alkyl or aryl lithium (n-butyl lithium, methyl lithium or phenyl lithium), an alkoxide (sodium methoxide or potassium t-butoxide), a hydrocarbylsubstituted ammonium hydroxide (benzyltrimethylammonium hydroxide), ammonium hydroxide, ammonia, etc. This can be done, for example, by suspending or dissolving the salt in a suitable liquid, such as water, an alcohol (ethanol or isopropanol), an aromatic (benzene or toluene), a hydrocarbon (hexane or heptane), etc. The reaction temperature can range from about room temperature to about 200° C., preferably from about room temperature to about 50° C., and the reaction time from about one minute to about four hours, or even longer, but preferably from about one to about two hours. Elevated pressures can be used, although atmospheric pressure will suffice. If the ylide obtained is a solid, recovery can be effected by filtration, decantation or by centrifuging. If the ylide is dissolved in the solvent, simple distillation is sufficient to remove the solvent, leaving behind the solid ylide. In some cases in association with the ylide so recovered will be the salt corresponding to the base that was used. For example, use of sodium hydroxide produces the corresponding sodium salt. The salt and the desired ylide can be separated from each other in any convenient manner, for example, by extraction with a solvent that will dissolve one and not the other. For example, aromatics, such as toluene, can be used to dissolve the ylide while water can be used to dissolve the salt. The ylide obtained can be defined by the following Formula IV:

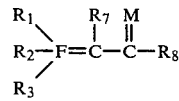

wherein $R_1$, $R_2$, $R_3$, $R_7$, $R_8$, F and M are as defined in Formula III.

The above identified ylide (Formula IV) is then reacted with (1) a ligand defined by the formula:

where $R_4$, $R_5$, and $R_6$ can be a hydrocarbyl, as defined above, a sulfonated hydrocarbyl or a sulfonato group, and E is as defined above; and (2) a zero valent nickel compound, or any nickel compound convertible to a zero valent nickel compound in situ, following the procedure of Procedure I. Specific examples of ligands that can be used include: allyldiphenylphosphine; benzyldiphenylphosphine; bis(3-aminopropyl)phenylphosphine; bis(2-cyanoethyl)phenylphosphine; bis(m-fluorophenyl)phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; di-allylphenylphosphine; di n-amylphenylphosphine; di-secbutylphenylphosphine; di-cyclohexylphenylphosphine; di-ethylphenylphosphine; di-n-heptylphenylphosphine; di-n-hexylphenylphosphine; dimethylphenylphosphine; dimethyl-p-tolylphosphine; diphenyl-n-butoxyphosphine; diphenylchlorophosphine; diphenylenephenylphosphine; diphenylethoxyphosphine; diphenylmethoxyphosphine; diphenylphosphine; beta-diphenylphosphinoethyltriethoxysilane; di-isopropylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyldi-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris-(m-chlorophenyl)phosphine; tris(p-chlorophenyl)phosphine; tri(1-naphthyl)phosphine; triphenylphosphine; tris(4-dimethylaminophenyl)phosphine; tris(p-fluorophenyl) phosphine; tris-(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphinebis(benzene-3-sulfonate); dimethylphenylarsine; methyldiphenylarsine; triphenylarsine; tri-p-tolylarsine; diphenylchloroarsine; triphenylantimony; triphenylamine; tribenzylamine; methyldiphenylamine; dimethylphenylamine; bis(2-cyanoethyl)phosphine; bis(dimethylamino)methylphosphine; t-butyldichlorophosphine; 2-cyanoethylphosphine; cyclohexylphosphine; di-t-butylchlorophosphine; dicyclohexylphosphine; diethylethoxyphosphine; diethyl-iso-propoxyphosphine; diethylphosphine; triallylphosphine; tri-iso-butylphosphine; tri-n-butylphosphine; tri-sec-butylphosphine; tri-t-butylphosphine; triethylphosphine; tri-n-hexylphosphine; trimethylphosphine; trifluorophosphine; tri-iso-propylphosphine; tri-n-propylphosphine; tris(2-cyanoethyl)phosphine; tris(dimethylamino)phosphine; tris(trimethylsilyl)phosphine; tri-n-butylantimony; triethylarsine; trimethylarsine; methyldiiodoarsine; trimethylamine; triethylamine; tributylamine; tripropylamine; dimethylamine; di-n-hexylamine; dicyclohexylamine; diethylamine; tricyclohexylamine; ammonia; and phosphine.

The following procedure, Procedure III, relates to the preparation of nickel ylides wherein the sulfonato group is in $R_7$. In the first step, the ylide defined by the following Formula V:

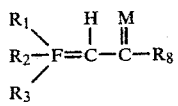

wherein each of $R_1$, $R_2$, $R_3$, and $R_8$ are hydrocarbyl radicals as defined above, and each of F and M is an element as defined above, is sulfonated to obtain the following sulfonated ylide defined by the following Formula IV:

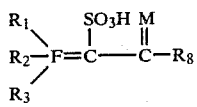

wherein each of $R_1$, $R_2$, $R_3$, $R_8$, M and F is as defised in Formula V. In some cases, for example, where $R_1$, $R_2$, $R_3$ and $R_8$ are phenyl, M is oxygen and F is phosphorus the following Formula VII may more accurately describe the structure:

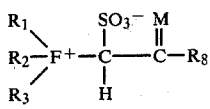

This first step can be done, for example, by dissolving the ylide of Formula V in a suitable solvent, for example, a halogenated hydrocarbon, such as chloroform, dichloroethane, methylene chloride or methyl chloroform, or a hydrocarbon solvent, such as heptane or hexane and then adding $SO_3$ to the resulting solution. The ylide and sulfonating agent are generally employed in equal molar amounts, although excess sulfonating agent can be present, if desired. Temperatures can be in the range of about 0° to about 200° C., preferably from about 20° to about 100° C., pressures can be elevated, although atmospheric pressure is preferred, and reaction times can vary from about five minutes to about 24 hours, preferably from about ten minutes to about four hours.

At the end of the reaction time the compounds defined by Formula VI or VII are recovered by any suitable means. If the sulfonated desired product is solid, recovery can be effected by filtration, decantation or by centrifuging. If the desired product is dissolved in the reaction medium, recovery can be effected by distillation to remove the solvent therefrom.

The sulfonated product is converted to the corresponding ylide by reacting the same with a base, such as an alkali metal hydroxide (sodium or potassium hydroxide), an alkyl or aryl lithium (n-butyl lithium, methyl lithium or phenyl lithium), an alkoxide (sodium methoxide or potassium t-butoxide), a hydrocarbyl-substituted ammonium hydroxide, (benzyltrimethylammonium hydroxide), ammonium hydroxide, ammonia, etc., to produce the following ylide defined by Formula VIII:

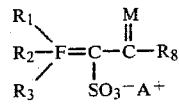

wherein $R_1$, $R_2$, $R_3$, $R_8$, F and M are as defined in Formula VI and A is the cationic portion of the base used. This can be done, for example, by suspending or dissolving the sulfonated ylide in a suitable liquid, such as water, an alcohol (ethanol or isopropanol), an aromatic (benzene or toluene), a hydrocarbon (hexane or heptane), etc. The reaction temperature can range from about room temperature to about 200° C., preferably from about room temperature to about 50° C., and the reaction time from about one minute to about four hours, or even longer, but preferably from about one to about two hours. Elevated pressures can be used, although atmospheric pressure will suffice. If the ylide obtained is a solid, recovery can be effected by filtration, decantation or by centrifuging. If the ylide is dissolved in the solvent, simple distillation is sufficient to remove the solvent, leaving behind the solid ylide.

The sulfonated ylide defined by Formula VIII is then reacted with (1) a ligand defined by the formula:

wherein $R_4$, $R_5$, and $R_6$ can be hydrocarbyl, as defined above, a sulfonated hydrocarbyl or a sulfate group, and E is as defined above; and (2) a zero valent nickel compound, or any nickel compound convertible to a zero valent nickel compound in situ, following the procedure of Procedure I. Specific examples of ligands that can be used include those previously set forth in Procedure II as examples of the ligand:

The following examples illustrate the invention, and are not intended to limit the invention, but rather, are presented for purposes of illustration. Examples I through III illustrate the preparation of nickel ylides useful in the process of this invention; and Example IV illustrates the use of ammonium hydroxide to remove nickel ylide residue from a solution thereof in toluene.

EXAMPLE I

This example is illustrative of Procedure I. To 20 milliliters of 30 percent fuming sulfuric acid there were added slowly with cooling 10 grams of triphenylphosphine. The solution was then heated to 80° C. and every five minutes the solution was tested by adding one drop of the solution to water until a clear solution was obtained. The reaction mixture was cooled to room temperature, poured into 200 cc of water and neutralized with 10 percent aqueous sodium hydroxide. After setting the solution overnight at room temperature, the desired product separated by crystallization and was recovered by filtration. The recovered product, sodium diphenylphosphinobenzene-3-sulfonate has the following structure:

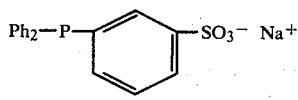
(Compound 1)

To 1.40 grams of bis(cyclooctadiene)nickel (5.1 millimoles) in 30 milliliters of toluene under an argon atmosphere there was added a solution of 1.86 grams of Compound 1 (5.1 millimoles) and 1.94 grams (5.1 millimoles) of benzoylmethylenetriphenylphosphorane:

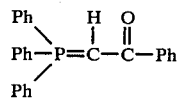
(Compound 2)

in 20 milliliters of toluene. After stirring for 18 hours at room temperature, the reaction mixture was heated to 50° C. to remove the solvent under a reduced pressure of 10 to 100 millimeters of mercury. The reaction mixture was transferred to an argon filled dry box and dissolved in toluene. Hexane was added to precipitate the product identified below as Compound 3. A total of 3.13 grams in 76 percent yield of the compound was recovered.

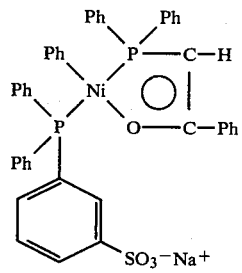
(Compound 3)

EXAMPLE II

This example is illustrative of Procedure II. To 4.65 grams of alpha-chloroacetophenone (0.03 mole) in 150 milliliters of toluene there were added 10.92 grams of Compound 1 (0.03 mole). This was heated to reflux under argon for five hours and then cooled and filtered. A total of 14.52 grams of the phosphonium salt:

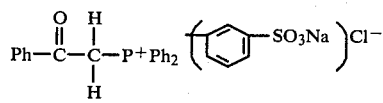
(Compound 4)

was obtained which was suspended in ethanol/water and titrated with 10 percent sodium hydroxide to a phenolphthalein end point. The ethanol was removed in vacuo and the product was washed with toluene to remove a small amount of unsubstituted benzoylmethylene triphenylphosphorane (1.2 grams). A total of 12.89 grams of the following phosphonium compound:

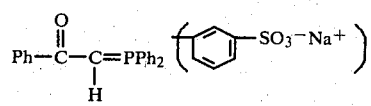
(Compound 5)

was obtained in 89 percent yield.

To 1.38 grams of bis(cyclooctadien)nickel (five millimoles) in 70 milliliters of tetrahydrofuran there was added a mixture of 1.31 grams of triphenylphosphine (five millimoles) and 2.41 grams of Compound 5 (five millimoles) dissolved in 70 milliliters of tetrahydrofuran. This was stirred at room temperature for 18 hours, after which the solvent was removed in vacuo. The resulting product was dissolved in toluene and filtered. Heptane was then added to precipitate the following nickel ylide:

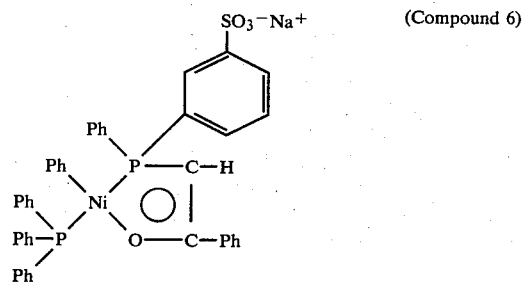
(Compound 6)

EXAMPLE III

This example is illustrative of Procedure III. To 4.01 grams of pyridine (0.05 mole) in 250 milliliters of dichlorethane there was added 6.97 grams of sulfur trioxide (0.87 mole) at 0° C. under nitrogen. After stirring for 0.5 hour, a solution of 19.05 grams of unsubstituted benzoylmethylenetriphenylphosphorane (0.05 mole) in 200 milliliters of dichloroethane was added. This was then heated to reflux for one hour. The reaction mixture was cooled to room temperature and the solvent removed in vacuo. The resulting product was then suspended in ethyl alcohol and filtered to give 19.7 grams of a white solid of the following phosphonium salt in 86 percent yield:

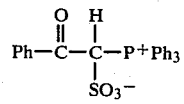
(Compound 7)

Compound 7 was also prepared as follows. To 29 grams of benzoylmethylenetriphenylphosphorane (0.076 mole) in 500 milliliters of dichloroethane at 25° C. under nitrogen there was added 5.47 milliliters of sulfur trioxide (0.132 mole). After stirring for 18 hours the solvent was removed in vacuo. Then 450 milliliters of ethanol and 50 milliliters of water were added and the mixture stirred for one-half hour. The produce was filtered and washed with ether to give 31.8 grams, 87 percent yield, of Compound 7.

Compound 7 was then suspended in water and titrated with 10 percent aqueous sodium hydroxide to a phenolphthalein end point. The water was then removed in vacuo and final traces removed via ethanol azeotrope to give 20.7 grams of the following ylide in 86 percent yield:

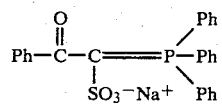 (Compound 8)

The nickel ylide, defined below as Compound 9, was prepared as follows. To 1.38 grams of bis(cyclooctadiene)nickel (five millimoles) in 30 milliliters of tetrahydrofuran there was added a mixture of 1.31 grams of triphenylphosphine (five millimiles) and 2.41 grams of Compound 8 (five millimoles) dissolved in 70 milliliters of tetrahydrofuran. The reaction mixture was stirred for 18 hours at room temperature, after which solvent was removed in vacuo. The resulting solid was dissolved in toluene and filtered. A yellow solid, which precipitated upon addition of heptane, was recovered by filtration. A total yield of 3.65 grams of Compound 9 was recovered in 91 percent yield.

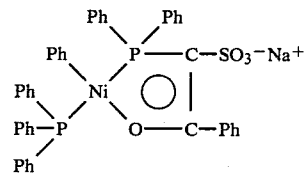 (Compound 9)

When Example III above was repeated except that Compound 7 was titrated with potassium hydroxide, ammonium hydroxide and trimethylphenylammonium hydroxide in place of 10 percent aqueous sodium hydroxide the following nickel ylides, respectively, were obtained:

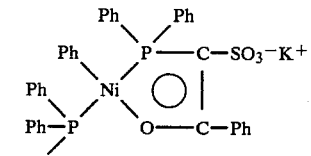 (Compound 10)

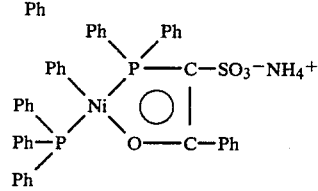 (Compound 11)

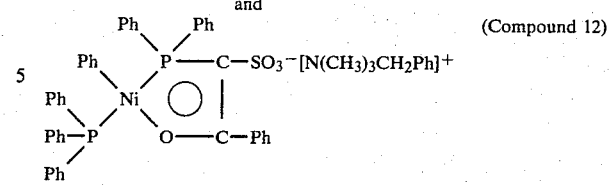 (Compound 12)

In producing Compounds 10, 11 and 12 identified above, it is apparent that the following ylides corresponding to Compound 8, respectively, will also be obtained:

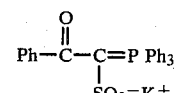 (Compound 13)

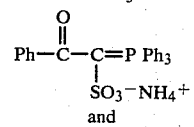 (Compound 14)

and

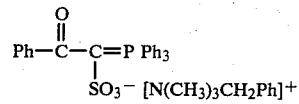 (Compound 15)

EXAMPLE IV

Into a reactor there was charged 0.08 gram (0.1 millimole) of the specific nickel ylide compound identified as Compound 9 in Example III hereof dissolved in 100 milliliters of toluene. To the resulting solution, there were added 100 milliliters of a 30 percent aqueous ammonium hydroxide solution. The resulting solution, which was maintained at 25° C., was agitated for one minute. Two separate and distinct liquid phases were formed, which were separated from each other in a separatory funnel and separately analyzed for their nickel and phosphorous content. Several additional runs were made similar to the above wherein the agitation time and the temperature of the solution were changed. Still additional runs were made using other solutions in place of ammonium hydroxide. The data obtained are summarized below in Table III.

TABLE III

| Run No. | Treating Solution | Agitation Time | Temp. °C. | Weight Percent Nickel | | Weight Percent Phosphorous | |
|---|---|---|---|---|---|---|---|
| | | | | Upper Layer | Lower Layer or Precipitate/ Emulsions | Upper Layer | Lower Layer or Precipitate/ Emulsion |
| I | 30% NH4OH | One Minute | 0 | <0.7 | >99.3 | 40.7 | 59.3 |
| II | 30% NH4OH | One Minute | 25 | 0.9 | 99.1 | 44.4 | 55.6 |
| III | 30% NH4OH | One Minute | 30 | 13.6 | 86.4 | 53.3 | 46.7 |
| IV | 30% NH4OH | One Hour | 25 | <0.7 | >99.3 | 45.3 | 54.7 |
| V | 30% NH4OH | Four Hours | 25 | <0.7 | >99.3 | 44.8 | 55.2 |
| VI | 30% NH4OH | 24 Hours | 25 | <0.7 | >99.3 | 46.0 | 54.0 |
| VII | 30% NH4OH | 72 Hours | 25 | <0.7 | >99.3 | 47.7 | 52.3 |
| VIII | 10% Aqueous NaOH | Four Hours | 25 | <1.5[a] | 98.5[a] | 44.4[a] | 55.6[a] |
| IX | 10% Aqueous KOH | Four Hours | 25 | <1.5[a] | 98.5[a] | 37.7[a] | 62.3[a] |
| X | 20% Aqueous NH4Cl | 72 Hours | 25 | 4.3[a] | 95.7[a] | 73.6[a] | 26.4[a] |
| XI | Water | 72 Hours | 25 | 6.7[a] | 93.3[a] | 61.2[a] | 38.8[a] |

[a]Emulsion or precipitate formed

In each of the above runs the toluene was in the upper phase and the treating solution in the lower phase. In each of Run Nos. I to VII two separate and distinct phases were obtained and no material precipitated out of solution that might have adversely affected the separation of the two phases from each other. It will be noted that the process is capable of removing substantially all of the nickel portion of the catalyst with the treating solution. In each of Run Nos. VIII and IX an emulsion formed intermediate the upper and lower layers, or phases, resulting in solutions which were difficult to separate. Runs with 30% NH$_4$OH, i.e., Runs I to VII, gave no emulsion and were easily separable. In Run No. X an appeciable amount of nickel residue was in the upper layer and an emulsion difficult to separate was also formed. Example XI was even less effective than Example X. Comparing Run Nos. I to VII with Run Nos. VIII to XI proves the uniqueness of ammonium hydroxide in the present process.

EXAMPLE V

Into a reactor there were charged about 0.04 gram of the specific nickel ylide compound identified as Compound 9 in Example III, about 50 milliliters of toluene and about 10 milliliters of a geometric distribution of alpha olefins from C$_4$ to C$_{40}$ produced by the oligomerization of ethylene in accordance with the process described in U.S. patent application Ser. No. 179,005, filed Aug. 18, 1980, entitled "Process for the Oligomerization of Ethylene in Methanol". There were then added 50 milliliters of a 30 percent aqueous ammonium hydroxide solution. The resultant solution was maintained at 25° C. and agitated for one minute. Two separate and distinct liquid phases were formed which were separated from each other in a separating funnel. Each phase was analyzed for its nickel and phosphorous content. The values found are reported in Table IV as Run No. XII. The behavior of this system was identical to Run Nos. I to VII using 30% NH$_4$OH where alpha olefins were not present, i.e., an emusion was not formed. An additional run was carried out by extraction of the above described solution of nickel ylide and alpha olefins in toluene with water instead of 30% aqueous NH$_4$OH. The results are reported in Table IV as Run No. XIII. The behavior of this system was identical to the results obtained in Run No. XI where alpha olefins were not present, i.e., an emulsion was formed.

tacting ethylene under oligomerization conditions with a nickel ylide defined by the following formula:

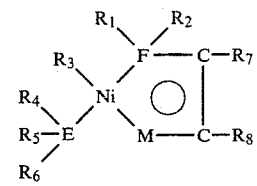

wherein R$_1$, R$_2$, R$_3$, R$_4$, R$_5$, R$_6$, R$_7$ and R$_8$ are either alike or different members selected from the group consisting of hydrogen, alkyl radicals having from about one to about 24 carbon atoms, aryl radicals having from about six to about 20 carbon atoms, alkenyl radicals having from about two to about 30 carbon atoms, cycloalkyl radicals having from about three to about 40 carbon atoms, aralkyl and alkaryl radicals having from about six to about 40 carbon atoms, halogen radicals, hydroxyl, alkoxy and aryloxy groups, and hydrocarbyl groups carrying halogen, hydroxyl, alkoxy or aryloxy groups, provided that at least one of each of R$_1$ to R$_8$ radicals is a sulfonato group or an alkyl, aryl, alkenyl, cycloalkyl, aralkyl or alkaryl carrying a sulfonato group, M is sulfur or oxygen, E is phosphorus, arsenic, antimony or nitrogen and F is phosphorus, arsenic or antimony, which comprises contacting said reaction product with ammonium hydroxide to obtain a product composed of two layers, an upper layer containing normal alpha olefins and a lower layer containing nickel ylide residue, and then separating said layers from each other to recover the desired normal alpha olefins.

2. A process as defined in claim 1 wherein the sulfonato group is in R$_4$, R$_5$ and/or R$_6$ and at least one of R$_4$, R$_5$ and R$_6$ is aryl.

3. A process as defined in claim 1 wherein the sulfonato group is in R$_1$, R$_2$ and/or R$_3$.

4. A process as defined in claim 1 wherein R$_7$ comprises a sulfonato group.

5. A process as defined in claim 1 wherein E and F are both phosphorus and M is oxygen.

6. A process as defined in claim 2 wherein E and F are both phosphorus and M is oxygen.

7. A process as defined in claim 3 wherein E and F are both phosphorus and M is oxygen.

TABLE IV

| Run No. | Treating Solution | Agitation Time | Temp. °C. | Weight Percent Nickel | | Weight Percent Phosphorous | |
|---------|-------------------|----------------|-----------|------------------------|------------------------------------------|------------------------|------------------------------------------|
| | | | | Upper Layer | Lower Layer or Precipitate/Emulsions | Upper Layer | Lower Layer or Precipitate/Emulsion |
| XII | 30% NH$_4$OH$^b$ | One Minute | 25 | <0.3 | >99.7 | 37.5 | 62.5 |
| XIII | H$_2$O$^b$ | One Minute | 25 | 1.2$^a$ | 98.8$^a$ | 48.0$^a$ | 52.0$^a$ |

$^a$Emulsion or precipitate formed
$^b$Toluene solution containing 20% by volume of geometric distribution of C$_4$—C$_{40}$ alpha olefins.

Although the invention has been described in considerable detail with particular reference to certain preferred embodiments thereof, variations and modifications can be effected within the spirit and scope of the invention as described hereinbefore, and as defined in the appended claims.

We claim:

1. A process for recovering normal alpha olefins from an oligomerization reaction product obtained by con- 8. A process as defined in claim 4 wherein E and F are both phosphorus and M is oxygen.

9. A process as defined in claim 6 wherein each of R$_4$, R$_5$ and R$_6$ is phenyl, one of which is substituted with a sulfonato group.

10. A process as defined in claim 9 wherein each of R$_1$, R$_2$, R$_3$ and R$_8$ is phenyl and R$_7$ is hydrogen.

11. A process as defined in claim 7 wherein each of R$_1$, R$_2$ and R$_3$ is phenyl, one of which is substituted with a sulfonato group.

12. A process as defined in claim 11 wherein each of $R_4$, $R_5$, $R_6$ and $R_8$ is phenyl and $R_7$ is hydrogen.

13. A process as defined in claim 8 wherein each of $R_1$, $R_2$, $R_3$, $R_4$, $R_5$, $R_6$ and $R_8$ is phenyl and $R_7$ is a sulfonato group.

14. A process as defined in claim 13 wherein said ylide is in the form of its sodium salt.

15. A process as defined in claim 1 wherein said ethylene and said nickel ylide are contacted in the presence of a solvent.

16. A process as defined in claim 13 wherein said ethylene and said nickel ylide are contacted in the presence of a solvent.

17. A process as defined in claim 14 wherein said ethylene and said nickel ylide are contacted in the presence of a solvent.

18. A process as defined in claim 15 wherein said solvent is selected from the group consisting of toluene, dioxane, tetrahydrofuran, anisole and methanol.

19. A process as defined in claim 16 wherein said solvent is selected from the group consisting of toluene, dioxane, tetrahydrofuran, anisole and methanol.

20. A process as defined in claim 17 wherein said solvent is selected from the group consisting of toluene, dioxane, tetrahydrofuran, anisole and methanol.

21. A process as defined in claim 1 wherein said ethylene and said nickel ylide are contacted at a temperature of from about −20° to about 200° C. for about one minute to about 72 hours.

22. A process as defined in claim 1 wherein said ethylene and said nickel ylide are contacted at a temperature of from about 20° to about 100° C. for about 10 minutes to about 24 hours.

23. A process as defined in claim 13 wherein said ethylene and said nickel ylide are contacted at a temperature of from about −20° to about 200° C. for about one minute to about 72 hours.

24. A process as defined in claim 13 wherein said ethylene and said nickel ylide are contacted at a temperature of from about 20° to about 100° C. for about 10 minutes to about 24 hours.

25. A process as defined in claim 14 wherein said ethylene and said nickel ylide are contacted at a temperature of from about −20° to about 200° C. for about one minute to about 72 hours.

26. A process as defined in claim 14 wherein said ethylene and said nickel ylide are contacted at a temperature of from about 20° to about 100° C. for about 10 minutes to about 24 hours.

27. A process as defined in claim 15 wherein said metal ylide is present in the range of about 0.0001 to about 1.0 mole per liter of solvent.

28. A process as defined in claim 15 wherein said metal ylide is present in the range of about 0.0005 to about 0.1 mole per liter of solvent.

29. A process as defined in claim 16 wherein said metal ylide is present in the range of about 0.0001 to about 1.0 mole per liter of solvent.

30. A process as defined in claim 16 wherein said metal ylide is present in the range of about 0.0005 to about 0.1 mole per liter of solvent.

31. A process as defined in claim 17 wherein said metal ylide is present in the range of about 0.0001 to about 1.0 mole per liter of solvent.

32. A process as defined in claim 17 wherein said metal ylide is present in the range of about 0.0005 to about 0.1 mole per liter of solvent.

33. A process as defined in claim 1 wherein the ethylene pressure is maintained in the range of about 10 to about 700 pounds per square inch gauge (68.9 to 4826 kPa) throughout the reaction.

34. A process as defined in claim 1 wherein the ethylene pressure is maintained in the range of about 300 to about 600 pounds per square inch gauge (2069 to 4137 kPa) throughout the reaction.

35. A process as defined in claim 1 wherein the ethylene pressure is maintained in the range of about 350 to about 550 pounds per square inch gauge (2413 to 3792 kPa) throughout the reaction.

36. A process as defined in claim 13 wherein the ethylene pressure is maintained in the range of about 10 to about 700 pounds per square inch gauge (68.9 to 4826 kPa) throughout the reaction.

37. A process as defined in claim 13 wherein the ethylene pressure is maintained in the range of about 300 to about 600 pounds per square inch gauge (2069 to 4137 kPa) throughout the reaction.

38. A process as defined in claim 13 wherein the ethylene pressure is maintained in the range of about 350 to about 550 pounds per square inch gauge (2413 to 3792 kPa) throughout the reaction.

39. A process as defined in claim 14 wherein the ethylene pressure is maintained in the range of about 10 to about 700 pounds per square inch gauge (68.9 to 4826 kPa) throughout the reaction.

40. A process as defined in claim 14 wherein the ethylene pressure is maintained in the range of about 300 to about 600 pounds per square inch gauge (2069 to 4137 kPa) throughout the reaction.

41. A process as defined in claim 14 wherein the ethylene pressure is maintained in the range of about 350 to about 550 pounds per square inch gauge (2413 to 3792 kPa) throughout the reaction.

42. A process as defined in claim 1 wherein at least about 0.1 milliliter of ammonium hydroxide, as 100 percent ammonium hydroxide, is contacted per 100 milliliters of said reaction product.

43. A process as defined in claim 1 wherein from about five to about 50 milliliters of ammonium hydroxide is contacted per 100 milliliters of said reaction product.

44. A process as defined in claim 13 wherein at least about 0.1 milliliter of ammonium hydroxide, as 100 percent ammonium hydroxide, is contacted per 100 milliliters of said reaction product.

45. A process as defined in claim 13 wherein from about five to about 50 milliliters of ammonium hydroxide is contacted per 100 milliliters of said reaction product.

46. A process as defined in claim 14 wherein at least about 0.1 milliliter of ammonium hydroxide, as 100 percent ammonium hydroxide, is contacted per 100 milliliters of said reaction product.

47. A process as defined in claim 14 wherein from about five to about 50 milliliters of ammonium hydroxide is contacted per 100 milliliters of said reaction product.

48. A process as defined in claim 1 wherein said ammonium hydroxide is aqueous ammonium hydroxide containing from about one to about 50 volume percent water.

49. A process as defined in claim 1 wherein said ammonium hydroxide is aqueous ammonium hydroxide containing from about 10 to about 35 volume percent water.

50. A process as defined in claim 13 wherein said ammonium hydroxide is aqueous ammonium hydroxide containing from about one to about 50 volume percent water.

51. A process as defined in claim 13 wherein said ammonium hydroxide is aqueous ammonium hydroxide containing from about 10 to about 35 volume percent water.

52. A process as defined in claim 14 wherein said ammonium hydroxide is aqueous ammonium hydroxide containing from about one to about 50 volume percent water.

53. A process as defined in claim 14 wherein said ammonium hydroxide is aqueous ammonium hydroxide containing from about 10 to about 35 volume percent water.

54. A process as defined in claim 1 wherein said ammonium hydroxide and said reaction product are agitated for at least about 10 seconds at a temperature of about 0° to about 30° C. and at a pressure of about 15 to about 2500 pounds per square inch gauge (103.4 to 17238 kPa).

55. A process as defined in claim 1 wherein said ammonium hydroxide and said reaction product are agitated for about one to about five minutes at a temperature of about 25° C. and at about atmospheric pressure.

56. A process as defined in claim 13 wherein said ammonium hydroxide and said reaction product are agitated for at least about 10 seconds at a temperature of about 0° to about 30° C. and at a pressure of about 15 to about 2500 pounds per square inch gauge (103.4 to 17238 kPa).

57. A process as defined in claim 13 wherein said ammonium hydroxide and said reaction product are agitated for about one to about five minutes at a temperature of about 25° C. and at about atmospheric pressure.

58. A process as defined in claim 14 wherein said ammonium hydroxide and said reaction product are agitated for at least about 10 seconds at a temperature of about 0° to about 30° C. and at a pressure of about 15 to about 2500 pounds per square inch gauge (103.4 to 17238 kPa).

59. A process as defined in claim 14 wherein said ammonium hydroxide and said reaction product are agitated for about one to about five minutes at a temperature of about 25° C. and at about atmospheric pressure.

60. A process as defined in claim 15 wherein said solvent is removed before said reaction product is contacted with said ammonium hydroxide.

61. A process as defined in claim 16 wherein said solvent is removed before said reaction product is contacted with said ammonium hydroxide.

62. A process as defined in claim 17 wherein said solvent is removed before said reaction product is contacted with said ammonium hydroxide.

* * * * *

UNITED STATES PATENT AND TRADEMARK OFFICE
CERTIFICATE OF CORRECTION

PATENT NO. : 4,301,318
DATED : November 17, 1981
INVENTOR(S) : David L. Beach and James J. Harrison It is certified that error appears in the above-identified patent and that said Letters Patent are hereby corrected as shown below:

Column 9, line 41, "XSO$_3$" should read --xSO$_3$--.

Column 14, line 33, "tris(O-methoxyphenyl)phosphine" should read --tris(o-methoxyphenyl)phosphine--.

Column 17, line 18, "IV" should read --VI--;
line 25, "defised" should read --defined--.

Column 18, line 34, "sulfate group" should read --sulfonato group--.

Column 20, line 8, "bis(cyclooctadien)nickel" should read --bis(cyclooctadiene)nickel--;
line 37, "(0.87 mole)" should read --(0.087 mole)--;
line 60, "produce" should read --product--.

Column 21, line 11, "(five millimiles)" should read --(five millimoles)--.

Signed and Sealed this

Fifth Day of October 1982

[SEAL]

Attest:

GERALD J. MOSSINGHOFF

Attesting Officer     Commissioner of Patents and Trademarks